United States Patent
Miyake et al.

(10) Patent No.: US 12,338,264 B2
(45) Date of Patent: Jun. 24, 2025

(54) CRYSTALLINE POTASSIUM SALT OF 2-O-α-D-GLUCOSYL-L-ASCORBIC ACID AND METHOD FOR PRODUCING THE SAME

(71) Applicant: NAGASE VIITA CO., LTD., Okayama (JP)

(72) Inventors: Akiko Miyake, Okayama (JP); Osamu Sano, Okayama (JP); Hirofumi Kunitake, Okayama (JP)

(73) Assignee: Nagase Viita Co., Ltd., Okayama (JP)

( * ) Notice: Subject to any disclaimer, the term of this patent is extended or adjusted under 35 U.S.C. 154(b) by 739 days.

(21) Appl. No.: 17/431,825

(22) PCT Filed: Feb. 6, 2020

(86) PCT No.: PCT/JP2020/004590
§ 371 (c)(1),
(2) Date: Aug. 18, 2021

(87) PCT Pub. No.: WO2020/170840
PCT Pub. Date: Aug. 27, 2020

(65) Prior Publication Data
US 2022/0153773 A1    May 19, 2022

(30) Foreign Application Priority Data
Feb. 20, 2019   (JP) ................................. 2019-028755

(51) Int. Cl.
*C07H 17/04*    (2006.01)
(52) U.S. Cl.
CPC .......... *C07H 17/04* (2013.01); *C07B 2200/13* (2013.01)
(58) Field of Classification Search
CPC ....... C07H 17/04; C07B 220/13; A23L 33/15; A61K 8/676
USPC .......................................................... 514/27
See application file for complete search history.

(56) References Cited

U.S. PATENT DOCUMENTS

| | | | |
|---|---|---|---|
| 5,137,723 | A | 8/1992 | Yamamoto et al. |
| 5,432,161 | A | 7/1995 | Sakai et al. |
| 2013/0172542 | A1 | 7/2013 | Shibuya et al. |
| 2015/0342854 | A1 | 12/2015 | Shibuya et al. |

FOREIGN PATENT DOCUMENTS

| | | | | |
|---|---|---|---|---|
| EP | 0 487 404 B1 | 10/1995 | | |
| EP | 0 461 827 B1 | 9/1997 | | |
| JP | 3-135992 A | 6/1991 | | |
| JP | 3-139288 A | 6/1991 | | |
| JP | 3-183492 A | 8/1991 | | |
| JP | 4-46112 A | 2/1992 | | |
| JP | 4-182412 A | 6/1992 | | |
| JP | 4-182413 A | 6/1992 | | |
| JP | 4-182419 A | 6/1992 | | |
| JP | 3290490 B2 | 6/2002 | | |
| JP | WO 2014/104171 A1 | * | 7/2014 | ............ A61K 8/676 |
| JP | 5856963 B2 | 2/2016 | | |
| JP | WO 2018/021542 A1 | * | 2/2018 | ............ C07H 17/04 |
| JP | 6307444 B2 | 4/2018 | | |
| WO | 2014/104171 A1 | 7/2014 | | |
| WO | 2018/021542 A1 | 2/2018 | | |

OTHER PUBLICATIONS

Hirayama, Noriaki, Handbook for preparing crystals of organic compounds, Yukikagoubutsu Kessyou Sakusei Handbook, 2008, pp. 17-23, 37-40, 45-51, 57-65, published by Maruzen Publishing Co., Ltd.
Takata, Noriyuki, API form screening and selection in drug discovery stage, Pharm Stage, vol. 6, No. 10, Jan. 15, 2007, pp. 20-25.
Wermuth, Medicinal Chemistry the second volume (Saishin Soyaku Kagaku Gekan), 1999, pp. 347-365, published by Technomics, Inc.
Japanese Decision of Refusal dated Nov. 15, 2023, from corresponding patent application No. JP2021-501848.

* cited by examiner

*Primary Examiner* — Ganapathy Krishnan
(74) *Attorney, Agent, or Firm* — FISHERBROYLES, LLP; Roger L. Browdy

(57) ABSTRACT

The present invention has objects to provide a novel crystalline 2-O-α-D-glucosyl-L-ascorbic acid and method for producing the same. The present invention solves the above objects by providing crystalline potassium salt of 2-O-α-D-glucosyl-L-ascorbic acid and method for producing the same.

8 Claims, 3 Drawing Sheets

CRYSTALLINE POTASSIUM SALT OF 2-O-α-D-GLUCOSYL-L-ASCORBIC ACID AND METHOD FOR PRODUCING THE SAME

TECHNICAL FIELD

The present invention relates to a novel crystalline potassium salt of 2-O-α-D-glucosyl-L-ascorbic acid and method for producing the same.

BACKGROUND ART

2-O-α-D-Glucosyl-L-ascorbic acid (abbreviated as "ascorbic acid 2-glucoside" throughout the specification, hereinafter) is a compound that is composed of one molecule of D-glucose bound to the hydroxyl group at the C-2 position of L-ascorbic acid (vitamin C) via the α-glucosidic linkage. Unlike L-ascorbic acid, ascorbic acid 2-glucoside is non-reducible and superior in stability and therefore it is also called "stable vitamin C". Ascorbic acid 2-glucoside is readily hydrolyzed by an in vivo enzyme into L-ascorbic acid and D-glucose in living bodies and exerts the physiological activities inherent to L-ascorbic acid.

Ascorbic acid 2-glucoside has been produced on an industrial scale by allowing cyclomaltodextrin glucanotransferase (abbreviated as "CGTase" throughout the specification, hereinafter) to act on a solution containing amylaceous substance and L-ascorbic acid and then allowing glucoamylase to act on the resulting solution (see, for example, Patent Literatures 1 to 3). A particulate composition containing anhydrous crystalline ascorbic acid 2-glucoside of high purity has been commercialized from the present applicant, Hayashibara Co., Ltd., Okayama, Japan, as "AA2G" (registered trademark), for use as a material for cosmetics/quasi-drugs, and mainly used extensively as a skin-whitening agent, etc., in the fields of cosmetics, quasi-drugs, etc. Also, it has been commercialized from the present applicant, Hayashibara Co., Ltd., Okayama, Japan, as "Ascofresh" (registered trademark), for use as a material for food and beverage (see, for example, Patent Literatures 4 to 7).

A variety of crystalline forms other than the above anhydrous crystals have also been reported. For example, Patent Literature 8 discloses hydrous crystalline ascorbic acid 2-glucsoide. In addition, Patent Literature 9 discloses two kinds of crystalline powders of aluminum salt and crystalline powder of zinc salt of ascorbic acid 2-glucoside, as crystalline metal salt of ascorbic acid 2-glucoside. Furthermore, Patent Literature 10 discloses hydrous and anhydrous crystalline sodium salt of ascorbic acid 2-glucoside. However, no other crystals of ascorbic acid 2-glucoside have been reported. Therefore, if novel crystalline ascorbic acid 2-glucoside or its salt would be provided, it is also very advantageous in terms of expanding the options for using ascorbic acid 2-glucoside in various fields.

PRIOR ART LITERATURE

Patent Literature

Patent Literature 1: Japanese Patent Kokai No. H03-139288
Patent Literature 2: Japanese Patent Kokai No. H03-135992
Patent Literature 3: Japanese Patent Kokai No. H03-183492
Patent Literature 4: Japanese Patent Kokai No. H04-046112
Patent Literature 5: Japanese Patent Kokai No. H04-182412
Patent Literature 6: Japanese Patent Kokai No. H04-182413
Patent Literature 7: Japanese Patent Kokai No. H04-182419
Patent Literature 8: Registered Japanese Patent No. 5856963
Patent Literature 9: Registered Japanese Patent No. 3290490
Patent Literature 10: Registered Japanese Patent No. 6307444

DISCLOSURE OF INVENTION

Object of the Invention

Objects of the present invention are to provide a novel crystalline salt of ascorbic acid 2-glucoside and method for producing the same.

Mean to Attain the Object

To solve the above objects, in the process of investigating the various conditions for crystallization of ascorbic acid 2-glucoside, the present inventors found that a crystal is precipitated when ascorbic acid 2-glucoside was dissolved in a potassium hydroxide aqueous solution of a specific concentration, alcohol was added to the solution and the solution was allowed to stand. When they subjected the obtained crystal to HPLC analysis, only peaks of ascorbic acid 2-glucoside was observed, and they subjected the crystal to powder X-ray diffractometry, it showed a powder X-ray diffraction pattern different from that of the previously known crystalline ascorbic acid 2-glucoside, indicating that the crystal was a novel crystalline ascorbic acid 2-glucoside.

The present invention solves the above objects by providing a novel crystalline potassium salt of ascorbic acid 2-glucoside and method for producing the same.

Effect of the Invention

According to the present invention, a novel crystalline potassium salt of ascorbic acid 2-glucoside can be provided. When the crystalline potassium salt of ascorbic acid 2-glucoside of the present invention is used in combination with anhydrous crystalline ascorbic acid 2-glucoside in the form of a mixture, the aqueous solution of the said mixture can be adjusted to the desired pH range without using alkali to neutralize the ascorbic acid 2-glucoside, which exhibits strong acidity, by appropriately controlling the mixing ratio of them. Therefore, the present invention can be advantageously used in the production of food and beverage, cosmetics, quasi-drugs, pharmaceuticals, and industrial goods.

MODE FOR CARRYING OUT THE INVENTION

Figure 1:
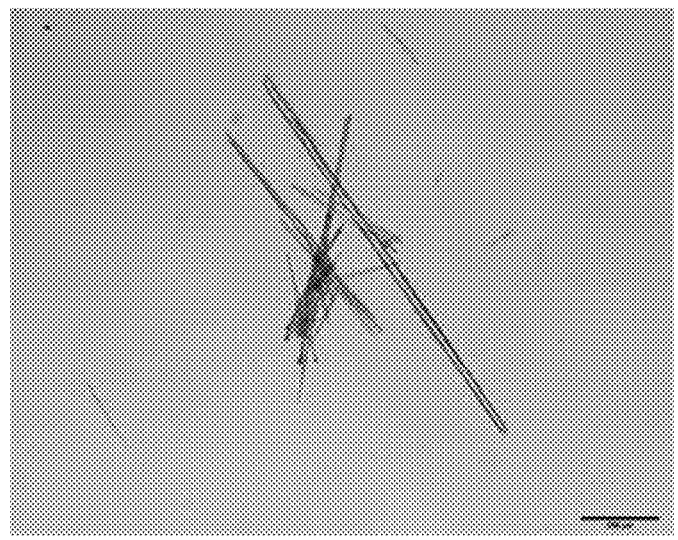
FIG. 1 An optical microscope photograph (125 magnifications) of the crystal obtained by adding methanol to a potassium hydroxide solution of ascorbic acid 2-glucoside.

The present invention relates to a novel crystalline potassium salt of ascorbic acid 2-glucoside. The crystal of the present invention is a completely novel crystal that the present inventors have independently discovered. As long as the crystal is a crystalline potassium salt of ascorbic acid 2-glucoside, and as long as it exhibits the physical properties and characteristics as crystalline potassium salt of ascorbic acid 2-glucoside disclosed in this application, it should never be restricted to a specific one produced by a particular method.

As shown in the experiment described later, the crystalline potassium salt of ascorbic acid 2-glucoside of the present invention is characterized in that it exhibits characteristic diffraction peaks at least at diffraction angles (2θ) of 8.27°, 8.81°, 16.05°, 18.88°, and 25.64°, when subjected to a powder X-ray diffractometry using a CuKα-ray as an X-ray source. The said powder X-ray diffraction pattern means that the crystal obtained in the present invention is crystal of ascorbic acid 2-glucoside, which is different from the conventionally known crystal of ascorbic acid 2-glucoside, because the powder X-ray diffraction pattern differs from all powder X-ray diffraction pattern of known anhydrous crystal, hydrous crystal, and crystalline sodium salt of ascorbic acid 2-glucoside.

As shown in the experiment described later, the crystalline potassium salt of ascorbic acid 2-glucoside of the present invention usually exhibits a moisture content of 12.5% to 14.8% by mass when measured by the conventional Karl Fisher method. This indicate that the crystalline potassium salt of ascorbic acid 2-glucoside of the present invention is in the form of hydrous crystal.

The crystalline potassium salt of ascorbic acid 2-glucoside usually contains 14.1% to 14.6% by mass of potassium when measured by ion chromatography in the experiment described later. From this result, it can be confirmed that the crystal of ascorbic acid 2-glucoside of the present invention is crystal of potassium salt.

Incidentally, as for the hydrous crystalline potassium salt of ascorbic acid 2-glucoside, the present inventors have also succeeded in obtaining a single crystal of a size that can be analyzed by single crystal X-ray structure analysis and also clarified that the crystal belongs to orthorhombic system, and the space group is $P2_12_12_1$; the lattice constant, a=7.6821 Å, b=12.726 Å, c=19.974 Å, and V=1952.7 (10) Å$^3$, by X-ray crystal structure analysis, as shown in the experiment described later.

The preset invention also provides a method for producing of the novel crystalline potassium salt of ascorbic acid 2-glucoside. The method for producing the hydrous crystalline potassium salt of ascorbic acid 2-glucoside can produce hydrous crystalline potassium salt of ascorbic acid 2-glucoside by dissolving ascorbic acid 2-glucoside as a material in a potassium hydroxide aqueous solution of a specific concentration, adding a specific amount of alcohol, allowing the resulting solution to stand at a low temperature to precipitate crystals, and collecting the precipitated crystals by using a solid-liquid separation method such as centrifugation.

In the method for producing of hydrous crystalline potassium salt of ascorbic acid 2-glucoside, the origin of ascorbic acid 2-glucoside as a material is not important, and it can be obtained by organic synthesis. In general, however, it is preferable to use an ascorbic acid 2-glucoside high content solution or "AA2G" (registered trademark), with a purity of ascorbic acid 2-glucoside at least 98% by mass, a product name of a quasi-drug grade of particulate composition containing anhydrous crystalline ascorbic acid 2-glucoside, commercialized by Hayashibara Co., Ltd., Okayama, Japan, or "Ascofresh" (registered trademark), with a purity of ascorbic acid 2-glucoside at least 98% by mass, a product name of a food grade particulate composition containing anhydrous crystalline ascorbic acid 2-glucoside, commercialized by Hayashibara Co., Ltd., Okayama, Japan, which prepared from the solution obtained by conventionally known method for producing of ascorbic acid 2-glucoside for food and beverage, or cosmetics; allowing CGTase to act on a solution containing amylaceous substance and L-ascorbic acid and then allowing glucoamylase to act on the resulting solution.

In the case of producing a crystalline potassium salt of ascorbic acid 2-gluclside using ascorbic acid 2-glucoside as a material, for example, the mass of one of anhydrous crystalline ascorbic acid 2-glucoside was dissolved by the addition of any of the 4 N to 8 N potassium hydroxide aqueous solutions in a ratio of liquid volume 2, then mixed by adding with alcohol in a ratio of liquid volume 3 or higher, and the mixed solutions allowed to stand at a low temperature, the hydrous crystalline potassium salt of ascorbic acid 2-glucoside will precipitate. For example, when using one gram of anhydrous crystalline ascorbic acid, the crystal was dissolved by adding with 2 mL of any of the 4 N to 8 N potassium hydroxide aqueous solution, then mixed by adding with 3 mL or higher of alcohol, and the mixed solutions allowed to stand at a low temperature. The molar ratio of potassium hydroxide to ascorbic acid 2-glucoside is usually in the range of 2.7 to 5.4, preferably, in the range of 3.4 to 4.1. The alcohols to be added in the operation to precipitate the crystals are not restricted, but methanol and ethanol, which are widely used in the art, are suitable for use. The alcohol concentration during crystallization should be around 50% by volume of the final concentration. The precipitated crystals can be collected by usual solid-liquid separation methods such as filtration and centrifugation.

The hydrous crystalline potassium salt of ascorbic acid 2-glucoside obtained by crystallization operation can be made into a higher purity crystal by washing the crystal with an alcohol aqueous solution. The obtained hydrous crystal can be made into a particulate composition containing hydrous crystalline potassium salt of ascorbic acid 2-glucoside by pulverizing and drying as necessary. A particulate composition containing hydrous crystalline potassium salt of ascorbic acid 2-glucoside can be obtained by spray-drying a massecuite prepared by adding an alcohol to precipitate crystals.

The hydrous crystalline potassium salt of ascorbic acid 2-glucoside of the present invention exhibit alkalinity when dissolved in water, as a characteristic feature. In this respect, it is the same as the known crystalline sodium salt of ascorbic acid 2-glucoside. This feature contrasts sharply with anhydrous crystalline ascorbic acid 2-glucoside that exhibits a relatively strong acidity when dissolved in water. Because of this, the novel crystalline potassium salt of ascorbic acid 2-glucoside created by the present inventors can be preferably used in various uses, where the amounts and the forms of use thereof and even the use thereof per se are restricted, because conventional anhydrous crystalline ascorbic acid 2-glucoside exhibits a relatively strong acidity when in an aqueous solution form. When used in soap-related external dermal compositions that require a slight alkalinity, for example, soaps, shampoos, cleansing foams, body soaps, etc., conventional particulate compositions containing anhydrous crystalline ascorbic acid 2-glucoside inevitably require a handling of neutralization of acid solutions of ascorbic acid 2-glucoside dissolved in an aqueous medium prior to use and also require the addition of buffer for pH control, but since aqueous solutions, obtained by dissolving crystalline potassium salt of ascorbic acid 2-glucoside in water, usually exhibit alkalinity and this would eliminate the need for a handling of neutralizing ascorbic acid 2-glucoside with an alkali, as well as often for the combination use with any buffer.

In the case of using hydrous crystalline potassium salt of ascorbic acid 2-glucoside in combination with anhydrous crystalline ascorbic acid 2-glucoside, an appropriate control of their composition ratio can provide, as a merit, an aqueous solution of ascorbic acid 2-glucoside with a pH within a prescribed pH range, for example, within a slightly alkaline to a slightly acidity range, when dissolved in an aqueous medium. When hydrous crystalline potassium salt of ascorbic acid 2-glucoside is used in combination with anhydrous crystalline ascorbic acid 2-glucoside, there can provide, as a merit, various compositions, which are preferably adjusted to give a pH ranging from a slightly alkaline pH to a slightly acidic pH as a whole, including the external dermal compositions and the basic skin cares, without using any additional alkali other than the hydrous crystalline potassium salt of ascorbic acid 2-glucoside. In using them both in combination, anhydrous crystalline ascorbic acid 2-glucoside and hydrous crystalline potassium salt of ascorbic acid 2-glucoside can be weighed in an amount corresponding to respective composition ratios before use, however, it is convenient to make them into compositions, which can be previously prepared by mixing anhydrous crystalline ascorbic acid 2-glucoside and hydrous crystalline potassium salt of ascorbic acid 2-glucoside in a prescribed composition ratio. In this case, the mass ratio can be set arbitrarily depending on the desired pH, but in order to achieve a weakly acidic to neutral range that is commonly used in cosmetics, it is usually suitable to combine in a ratio of 70:30 to 45:55, preferably 50:50 to 45:55 by mass.

The crystalline potassium salt of ascorbic acid 2-glucoside is a novel crystalline form of ascorbic acid 2-glucoside, and is similar to the known crystalline sodium salt of ascorbic acid 2-glucoside in that the pH of its aqueous solution exhibits alkalinity. The crystalline potassium salt of ascorbic acid 2-glucoside of the present invention can also be advantageously used in production of food and beverage, cosmetics, quasi-drugs, pharmaceuticals, and industrial goods containing ascorbic acid 2-glucoside, as well as the anhydrous crystal, hydrous crystal, and crystalline sodium salt of ascorbic acid 2-glucoside, which are conventionally known.

The following experiments explain the present invention in detail.

Experiment 1: Preparation of Crystalline Potassium Salt of Ascorbic Acid 2-Glucoside Twelve grams of particulate composition containing anhydrous crystalline ascorbic acid 2-glucoside (product name "Ascofresh" (registered trademark), commercialized by Hayashibara Co., Ltd., Okayama, Japan), was dissolved in 24 mL of 5 N potassium hydroxide solution, admixed with an additional 36 mL of methanol to this solution, stirred, and allowed to stand for four days at 4° C., resulting in a formation of white turbidity and precipitation of crystals upon microscopic observation. The formed suspension with crystals was filtered with Kiriyama Rhoto (commercialized by Kiriyama Glass Works Co., Tokyo, Japan) (ADVANTEC No. 5, commercialized by Toyo Roshi Kaisha, Ltd., Tokyo, Japan, is used) to collect the precipitated crystals, which were then washed with deionized water and vacuum dried for five hours at 30° C. to obtain an about 15.4 g crystalline powder. The molar ratio of potassium hydroxide to ascorbic acid 2-glucoside in the solution was 3.4.

Experiment 2: Analyses on Novel Crystalline Ascorbic Acid 2-Glucoside

The crystal obtained in Experiment 1 was observed microscopically for crystalline forms, subjected to HPLC analysis, and measured for pH of the solution, UV absorption spectroscopy, powder X-ray diffraction pattern, moisture content, and potassium content.

Experiment 2-1: Crystalline Form

The crystal obtained in Experiment 1 was observed for crystalline form by using an optical microscope. The crystal obtained in Experiment 1 was 10~100 μm×1000 μm in size, and had a columnar-crystal form and it was transparent. Micrograph of a typical crystal among those obtained was taken and shown in FIG. 1. The length of the scale bar shown in the lower right corner of FIG. 1 is 200 μm.

Experiment 2-2: HPLC Analysis

The crystal obtained in Experiment 1 was dissolved in deionized water to a final concentration of 1% by mass and subjected to the following conditions for HPLC analysis. As a control, "Ascofresh" (registered trademark), a product name of a food grade particulate composition containing anhydrous crystalline ascorbic acid 2-glucoside, commercialized by Hayashibara Co., Ltd., Okayama, Japan, was analyzed under the same conditions as above.
<Conditions for HPLC Analysis>
    Column: "Wakopak Wakobeads T-330 H-form",
        10 mm in inner diameter×300 mm in length,
        Wako Pure Chemical Co., Ltd., Tokyo, Japan
    Eluent: 0.0001 N nitric acid aqueous solution
    Flow rate: 0.4 mL/min
    Temperature: Ambient temperature
    Detection: Refractive index detector In the HPLC chromatogram of the test sample solution in which the crystal was dissolved, almost only the peak of ascorbic acid 2-glucoside was detected, as in the case of the powder containing ascorbic acid 2-glucoside anhydrous crystal used as a control, confirming that the crystal obtained in Experiment 1 was crystalline ascorbic acid 2-glucoside.

Experiment 2-3: H and UV Absorption Spectra of the Aqueous Solution in which the Crystal was Dissolved 1% by mass of aqueous solution of the crystal obtained in Experiment 1 was prepared and its pH was measured. The pH of the aqueous solution was 12.7, indicating alkalinity. When the aqueous solution was diluted 300 folds and the UV spectrum of the diluted aqueous solution was measured, it showed the same UV absorption spectrum (λmax 260 nm) as ascorbic acid 2-glucoside.

Experiment 2-4: Powder X-Ray Diffraction Pattern

The crystal obtained in Experiment 1 was subjected to powder X-ray diffraction analysis using a powder X-ray diffractometer ("X' Pert Pro MPD", a product name of a powder X-ray diffractometer commercialized by Spectris Co., Ltd., Tokyo, Japan, using CuKα-ray). About 50 mg of the crystal sample were placed on a silicon reflection free plate, irradiated with a CuKα-ray under the following conditions while rotating, and determined for powder X-ray diffraction pattern by a reflection method. The obtained powder X-ray diffraction pattern is shown in FIG. 2.

<Conditions for Irradiating CuKα-Ray>
X-Ray tube current: 40 mA
X-Ray tube voltage: 45 kV
Wavelength: 1.5405 Å

Figure 3:
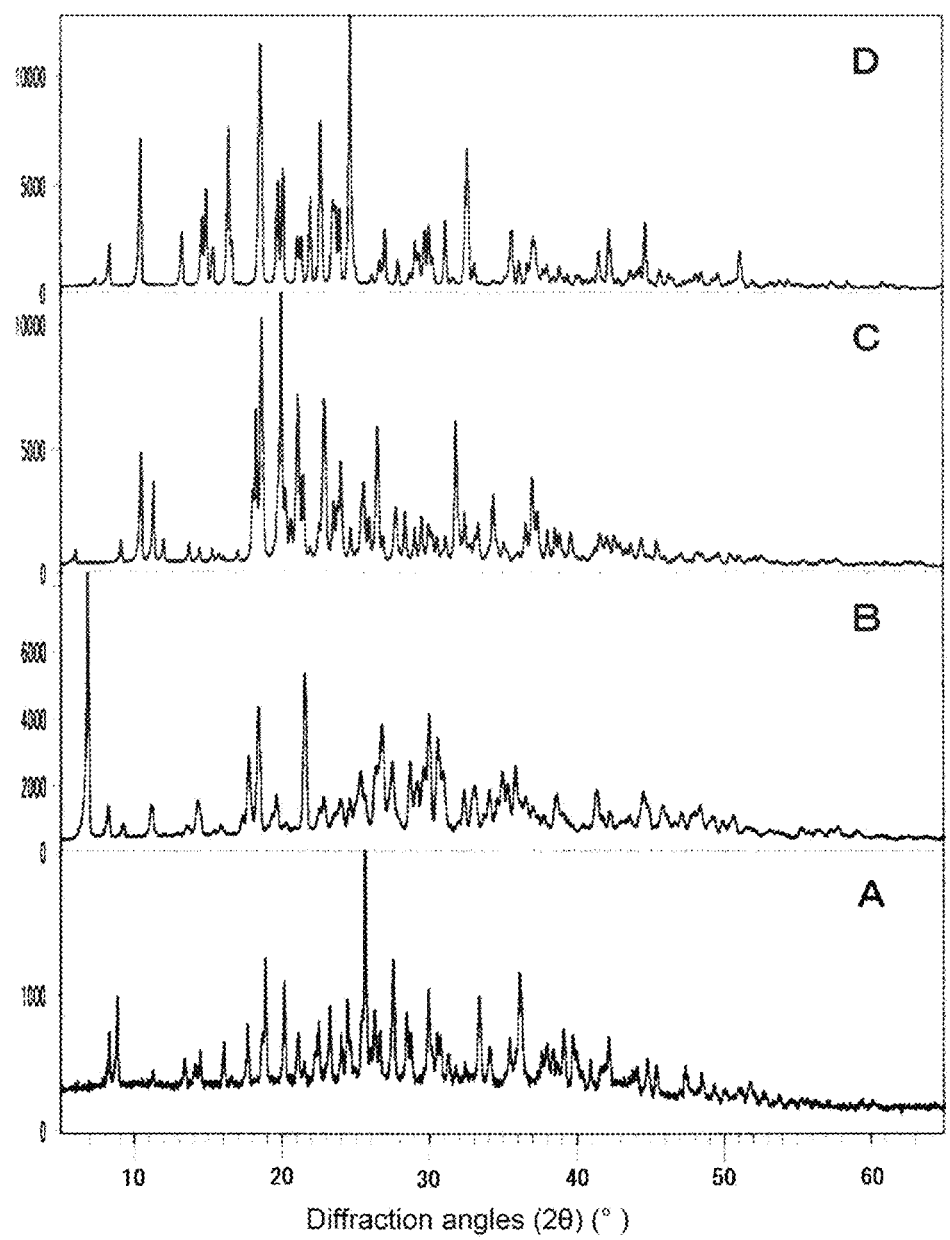
FIG. 3 A figure of the crystal shown in FIG. 2, contrasted with patterns of anhydrous crystal, hydrous crystal, and crystalline sodium salt of ascorbic acid 2-glucoside (hydrous crystal).

The powder X-ray diffraction patterns of newly obtained crystal and that of known crystalline ascorbic acid 2-glucoside are shown together in FIG. 3. In FIG. 3, the powder X-ray diffraction patterns of the crystal obtained in Experiment 1, the crystalline sodium salt of ascorbic acid 2-glucoside (hydrous crystal prepared by Hayashibara Co., Ltd., Okayama, Japan), the hydrous crystalline ascorbic acid 2-glucoside (prepared by Hayashibara Co., Ltd., Okayama, Japan), and the anhydrous crystalline ascorbic acid 2-glucoside ("Ascofresh" (registered trademark), a product name of a particulate composition containing anhydrous crystalline ascorbic acid 2-glucoside, commercialized by Hayashibara Co., Ltd., Okayama, Japan) are indicated by symbols A, B, C, and D, respectively.

Figure 2:
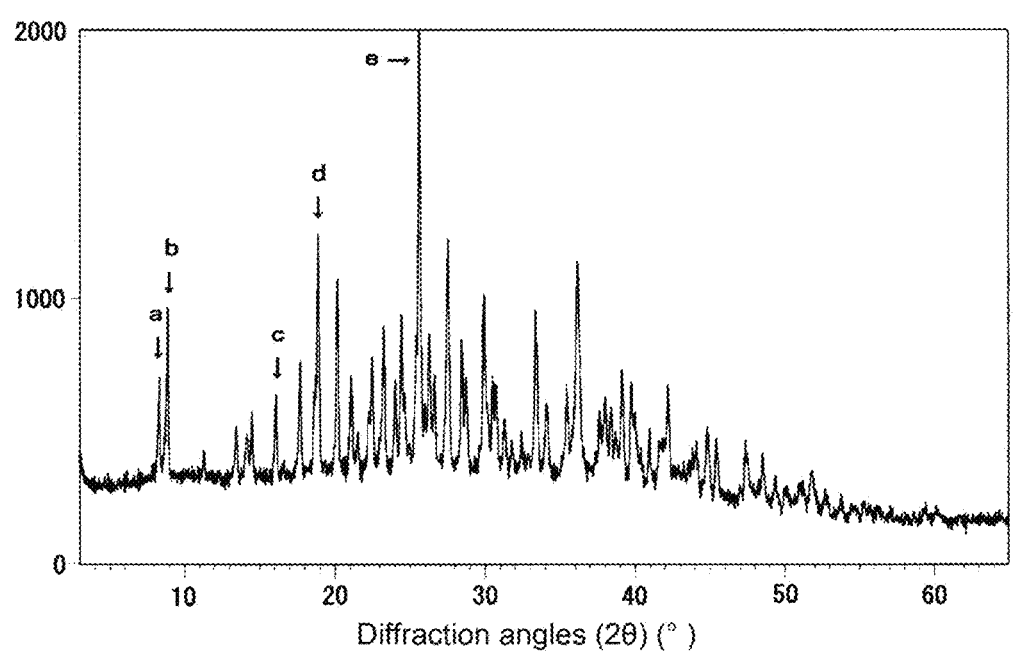
FIG. 2 A powder X-ray diffraction pattern of the crystal obtained by adding methanol to a potassium hydroxide solution of ascorbic acid 2-glucoside.

As shown in FIG. 2, the newly obtained crystal exhibited characteristic diffraction peaks at diffraction angles (2θ) of 8.27°, 8.81°, 16.05°, 18.88°, and 25.64° (symbols a, b, c, d, and e in FIG. 2) in the powder X-ray diffraction pattern. In addition, as shown in FIG. 3, the powder X-ray diffraction pattern completely different from those of conventionally known anhydrous crystalline ascorbic acid 2-glucoside, the hydrous crystalline ascorbic acid 2-glucoside, or crystalline sodium salt of ascorbic acid 2-glucoside (hydrous crystal). These results revealed that the crystal obtained in Experiment 1 is novel crystalline ascorbic acid 2-glucoside.

Experiment 2-5: Measurement of Moisture Content

The moisture content of the crystal obtained in Experiment 1 was measured using a Karl Fischer moisture analyzer ("AQ-2200" a product name commercialized by Hiranuma sangyo Co., Ltd., Ibaraki, Japan), revealing that it had 14.8% by mass of moisture. This result indicated that the novel crystalline ascorbic acid 2-glucoside obtained in Experiment 1 was in the form of hydrous crystal.

Experiment 2-6: Measurement of Potassium Content

One hundred fifty milligrams of the crystal obtained in Experiment 1 was weighted, dissolved in 100 mL of deionized water, and further diluted 50 folds with deionized water for use as a sample for measurement. Potassium content in the sample was measured under the following conditions with an ion chromatograph ("DIONEX ICS-5000+", a product name commercialized by Thermo Fisher Scientific Co., Ltd., Tokyo, Japan), <Conditions of Measurement>
Column: "Dionex IonPac CS16",
  5 mm in inner diameter×250 mm in inner diameter x, Thermo Fisher Scientific Co., Ltd., Tokyo, Japan
Guard Column: "Dionex IonPac CS16 Guard"
  5 mm in inner diameter×50 mm in inner diameter x, Thermo Fisher Scientific Co., Ltd., Tokyo, Japan
Eluent: 30 mM methane sulfonic acid
Flow rate: 1.0 mL/min
Temperature: 40° C.
Detection: Electrical conductivity detector
Suppressor: Electric field regeneration type CERS-500
Electric current: 89 mA
Detector compartment temperature: 20° C.
Sample dosage: 25 μL
Standard solution: Cation mixed standard solution II
  (6 kinds of mixture) for IC No. 07197-96
    Kanto Chemical Co., Ltd., Tokyo, Japan The potassium content of the crystal, calculated based on the result of ion chromatography, was 14.2% by mass. The result confirmed that the crystalline ascorbic acid 2-glucoside obtained in Experiment 1 was potassium salt crystal.

Incidentally, the composition of the crystal (% by mass), calculated on the assumption that potassium exists as potassium hydroxide (KOH) in the crystal, is shown in Table 1. Furthermore, the molar ratio of ascorbic acid 2-glucoside to potassium hydroxide in such a case is calculated and the results are also shown in Table 1.

TABLE 1

| | Composition | | |
|---|---|---|---|
| | Ascorbic acid 2-glucoside | Potassium hydroxide (KOH) | Water |
| Mass (%) | 64.8 | 20.4 | 14.8 |
| Molar ratio | 1.0 | 1.9 | 4.3 |

As described above, the hydrous crystalline potassium salt of ascorbic acid 2-glucoside has a potassium content of about 14.2% by mass. Based on the assumption that all potassium exists as potassium hydroxide (KOH) in the crystal, the potassium hydroxide content in the crystal was calculated to be 20.4% by mass. In this case, subtracting the mass of water (14.8% by mass) and the mass of potassium hydroxide (20.4% by mass) from the mass of the crystal (100% by mass), the amount of ascorbic acid 2-glucoside in the crystal is 64.8% by mass. Based on these values, the molar ratios of ascorbic acid 2-glucoside and potassium hydroxide were calculated. As shown in Table 1, these molar ratios were 1.0:1.90, therefore, assuming that all potassium exhibits in the form of potassium hydroxide in the crystal, it is estimated that the hydrous crystalline potassium salt of ascorbic acid 2-glucoside contains about two molecules of potassium hydroxide per one molecule of ascorbic acid 2-glucoside.

Similarly, the hydrous crystalline potassium salt of ascorbic acid 2-glucoside has a moisture content of about 14.8% by mass, and the molar ratio of ascorbic acid 2-glucoside to water is about 1.0:4.3. From this, it is estimated that the hydrous crystalline potassium salt of ascorbic acid 2-glucoside contains about four molecules of crystallization water per one molecule of ascorbic acid 2-glucoside.

These results in Experiments 2-1 to 2-6 confirmed that the crystal obtained in Experiment 1 is a hydrous crystalline potassium salt of ascorbic acid 2-glucoside.

Experiment 3: Study on the Formation Condition of Crystalline Potassium Salt of Ascorbic Acid 2-Glucoside One gram of particulate composition containing anhydrous crystalline ascorbic acid 2-glucoside (product name "Ascofresh" (registered trademark), commercialized by Hayashibara Co., Ltd., Okayama, Japan), was dissolved by the addition of 2 mL of any of the 1 N to 10 N potassium hydroxide aqueous solutions shown in the following Table 2, added with 3 mL of methanol and mixed. The mixed solutions allowed to stand at 4° C. for 24 hours, followed by macroscopically observing the degree crystal precipitation. The degree of crystal precipitation was judged based on the following four grades:

"−": No crystal precipitation;
"+": Slight crystal-precipitation;
"++": Crystal precipitation in an amount roughly equal to half of the total volume; and
"+++": Crystal precipitation and solidification throughout the whole content.

The results are in Table 2.

TABLE 2

| Particulate composition containing anhydrous crystalline ascorbic acid 2-glucoside (g, on a dry solid basis) | Potassium hydroxide aqueous solution Concentration (N) | Liquid volume (mL) | Potassium hydroxide/ Ascorbic acid 2-glucoside (molar ratio) | Methanol Liquid volume (mL) | Crystal precipitation |
|---|---|---|---|---|---|
| 1 | 10 | 2 | 6.8 | 3 | − |
| 1 | 8 | 2 | 5.4 | 3 | + |
| 1 | 6 | 2 | 4.1 | 3 | ++ |
| 1 | 5 | 2 | 3.4 | 3 | +++ |
| 1 | 4 | 2 | 2.7 | 3 | + |
| 1 | 3 | 2 | 2.0 | 3 | − |
| 1 | 2 | 2 | 1.4 | 3 | − |
| 1 | 1 | 2 | 0.7 | 3 | − |

As shown in Table 2, precipitations of crystalline potassium salt of ascorbic acid 2-glucoside were observed from respective potassium hydroxide aqueous solutions, which had been prepared by dissolving a particulate composition containing anhydrous crystalline ascorbic acid 2-glucoside in any of 4 N, 5 N, 6 N, and 8 N potassium hydroxide aqueous solutions and admixing each of the resulting solutions with methanol. Regarding the molar ratio of potassium hydroxide to ascorbic acid 2-glucoside, crystal precipitations were observed when the molar ratio was in the range of 2.7 to 5.4. On the other hand, when the potassium hydroxide concentration was 3 N or lower, that is, the molar ratio of potassium hydroxide to ascorbic acid 2-glucoside was 2.0 or lower, no crystal precipitation was observed. Also, when the potassium hydroxide concentrations 10 N or higher, that is, the molar ratio of potassium hydroxide to ascorbic acid 2-glucoside was 6.8 or higher, no crystal precipitation was observed, and the samples were colored.

The Patent Literature 10 discloses a method for producing a crystalline sodium salt of ascorbic acid 2-glucoside. According to the that, the crystal precipitation was observed when the molar ratio of sodium hydroxide to ascorbic acid 2-glucoside was 1.7 or higher, and the amount of methanol for 1 g of ascorbic acid 2-glucoside was 1 mL. In producing the crystalline potassium salt of ascorbic acid 2-glucoside, the present inventors first attempted to precipitate the crystals under the same precipitation conditions for the sodium salt crystals disclosed in Patent Literature 10, except for replacing sodium hydroxide with potassium hydroxide. However, the crystalline potassium salt of ascorbic acid 2-glucoside could not be obtained. That is, ten grams of particulate composition containing anhydrous crystalline ascorbic acid 2-glucoside (product name "AA2G" (registered trademark), commercialized by Hayashibara Co., Ltd., Okayama, Japan), was dissolved by the addition of 10 mL of 8 N potassium hydroxide aqueous solution, added with 10 mL of methanol and mixed, then the mixed solutions allowed to stand at 4° C. for 24 hours, but no crystalline potassium salt of ascorbic acid 2-glucoside could be obtained. As a result of trial and error, the inventors of the present invention surprisingly succeeded in precipitating the crystalline potassium salt of ascorbic acid 2-glucoside by adding 3 times as much the amount of methanol as for sodium salt crystals. Thus, the crystalline potassium salt of ascorbic acid 2-glucoside of the present invention is obtained under completely different conditions from those for the crystalline sodium salt of ascorbic acid 2-glucoside.

Experiment 4: pH of a Composition of Crystalline Potassium Salt of Ascorbic Acid 2-Glucoside and Anhydrous Crystalline Ascorbic Acid 2-Glucoside A commercially available particulate composition containing anhydrous crystalline ascorbic acid 2-glucoside (product name "Ascofresh" (registered trademark), commercialized by Hayashibara Co., Ltd., Okayama, Japan) and a hydrous crystalline potassium salt of ascorbic acid 2-glucoside, obtained by the method in the Experiment 1 were made into compositions with the ratios by mass ranging from 100:0 to 0:100 as shown in Table 3. Each of the resulting compositions was dissolved in deionized water to give a concentration of 1% by mass, following by measuring the pHs of the resulting solutions. The results are shown in Table 3.

TABLE 3

| Percentage of anhydrous crystalline ascorbic acid 2-glucoside (% by mass) | Percentage of hydrous crystalline potassium salt of ascorbic acid 2-glucoside (% by mass) | pH of 1% by mass aqueous solution |
|---|---|---|
| 100 | 0 | 2.2 |
| 90 | 10 | 2.5 |
| 80 | 20 | 2.8 |
| 70 | 30 | 3.0 |
| 60 | 40 | 3.4 |
| 55 | 45 | 3.8 |
| 50 | 50 | 4.4 |
| 45 | 55 | 7.0 |
| 40 | 60 | 11.6 |
| 30 | 70 | 12.2 |
| 20 | 80 | 12.4 |
| 10 | 90 | 12.6 |
| 0 | 100 | 12.7 |

As shown in Table 3, the aqueous solution prepared by dissolving the particulate composition containing anhydrous crystalline ascorbic acid 2-glucoside alone (100% by mass) in water to give a concentration of 1% by mass had a pH of 2.2, while the aqueous solution prepared by dissolving the hydrous crystalline potassium salt of ascorbic acid 2-glucoside alone (100% by mass) in water to give a concentration of 1% by mass had a pH of 12.7. Also, the aqueous solution prepared by changing the compound ratio of the particulate composition containing anhydrous crystalline ascorbic acid 2-glucoside and the hydrous crystalline potassium salt of ascorbic acid 2-glucoside in the range of 90:10 to 10:90 to give a concentration of 1% by mass exhibited pHs in the range of 2.5 to 12.6, From these results, it was found that the aqueous solutions can be made to give desired pHs ranging widely from acidic pHs and alkaline pHs by combining particulate composition containing anhydrous crystalline ascorbic acid 2-glucoside and hydrous crystalline potassium salt of ascorbic acid 2-glucoside in appropriate mass ratios, particularly, when combined in mass ratios ranging from 70:30 to 45:55, the pHs can be adjusted in the range of 3.0:7.0, and more particularly, when combined in mass ratios ranging from 50:50 to 45:55, the pHs can be adjusted in the range of 4.4 to 7.0, in which exhibit a weakly acidic to neutral range.

Experiment 5: Hygroscopicity of Hydrous Crystalline Potassium Salt of Ascorbic Acid 2-Glucoside An experiment was carried out to compare the hygroscopicity of both the hydrous crystalline potassium salt of ascorbic acid 2-glucoside, obtained by the method in the Experiment 1, and the hydrous crystalline sodium salt of ascorbic acid 2-glucoside, obtained by the method described in Patent Literature 10. That is, 0.5 g each of the hydrous crystalline potassium salt of ascorbic acid 2-glucoside and the hydrous crystalline sodium salt of ascorbic acid 2-glucoside were weighted and stored in a desiccator conditioned to 75.2% relative humidity (RH) using saturated salt solution for 24 hours at room temperature. After that, the mass of each was measured, the mass increased by moisture absorption was determined, and the increase rate of mass {(Mass increased by storage)/(Mass at the beginning of storage)×100} (% by mass) was determined. The results are shown in Table 4.

TABLE 4

| Test sample | Increase rate of mass * (% by mass) |
|---|---|
| Hydrous crystalline potassium salt of ascorbic acid 2-glucoside | 9.1 |
| Hydrous crystalline sodium salt of ascorbic acid 2-glucoside | 15.8 |

* relative humidity 75.2%, at room temperature, after storage for 24 hours

As shown in Table 4, the hydrous crystalline potassium salt of ascorbic acid 2-glucoside and the hydrous crystalline sodium salt of ascorbic acid 2-glucoside exhibited respectively a increase rate of mass of 9.1% by mass and 15.8% by mass in this study, it was revealed that both crystals absorb moisture at a relative humidity (RH) of 75.2%. The increase rate of mass of the hydrous crystalline potassium salt of ascorbic acid 2-glucoside was just under 60% of that of the hydrous crystalline sodium salt of ascorbic acid 2-glucoside, indicating that the hydrous crystalline potassium salt of ascorbic acid 2-glucoside exhibited less hygroscopicity than the hydrous crystalline sodium salt of ascorbic acid 2-glucoside.

Experiment 6: Single Crystal X-Ray Crystallography of Hydrous Crystalline Potassium Salt of Ascorbic Acid 2-Glucoside Crystallization was carried out over time under condition which crystals are less likely to precipitate than usual to obtain relatively large crystals that could be used for single crystal X-ray crystallography. That is, one gram of particulate composition containing anhydrous crystalline ascorbic acid 2-glucoside (product name "Ascofresh" (registered trademark), commercialized by Hayashibara Co., Ltd., Okayama, Japan) was dissolved in 2 mL of 4N potassium hydroxide solution, which is low concentrated than normal crystallization, added with 3 mL of methanol, mixed, and crystallized for 4 days to precipitate crystals of hydrous crystalline potassium salt of ascorbic acid 2-glucoside. From among the obtained crystals, a crystal with appropriate size (0.30×0.09×0.07 mm) was selected and measured for X-ray diffraction patterns using an X-ray diffractometer ("RIGAKU VariMax with Saturn 724", commercialized by Rigaku Corporation, Tokyo, Japan) under the following conditions. For the analysis software, "Crystal Clear", commercialized by Rigaku Corporation, Tokyo, Japan, was used.

<Conditions for Measurement>
  Incident X-ray: MoKα-ray (wavelength: 0.71075 Å)
  Power: 50 kV-24 mA
  Detector: Imaging plate
  Measurement temperature: About −173° C. (nitrogen gas blowing method)

In the X-ray diffraction pattern of the crystal on the imaging plate, a plenty of diffraction mottles (spots) were observed, revealing that the crystal was a single crystal. Table 5 is a summary of crystallographic parameters of hydrous crystalline potassium salt of ascorbic acid 2-glucoside, obtained by the single crystal X-ray crystallography,

TABLE 5

| Crystalline system | Lattice constant | Space group |
|---|---|---|
| Orthorhombic system | a = 7.6821 Å<br>b = 12.726 Å<br>c = 19.974 Å<br>V = 1952.7 (10) Å$^3$ | P2$_1$2$_1$2$_1$ |

From the obtained data on X-ray diffraction strength, as shown in Table 5, it was determined that the hydrous crystalline potassium salt of ascorbic acid 2-glucoside belongs to orthorhombic system, and the space group is P2$_1$2$_1$2$_1$; the lattice constant, a=7.6821 Å, b=12.726 Å, c=19.974 Å, and V=1952.7 (10) Å$^3$.

Figure 4:
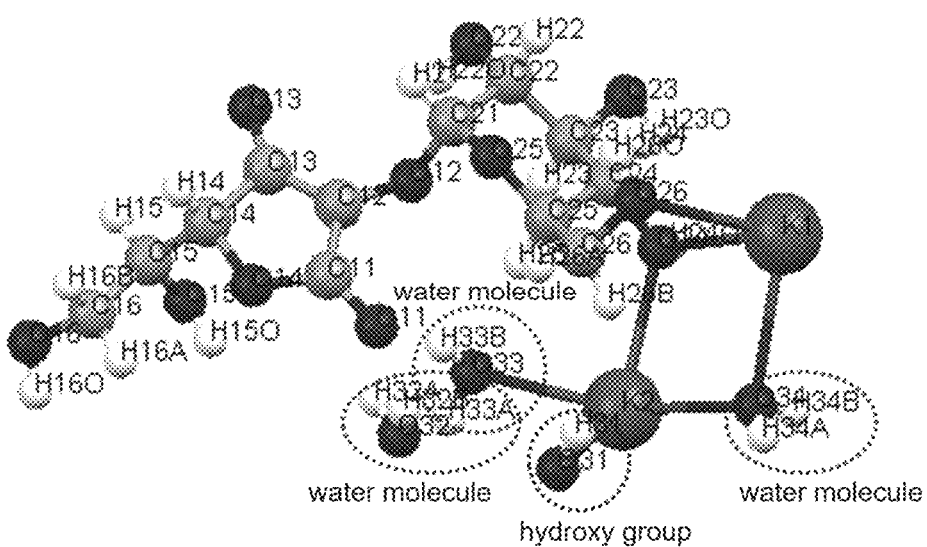
FIG. 4 An ORTEP figure of the hydrous crystalline potassium salt of ascorbic acid 2-glucoside obtained by single-crystal X-ray structure analysis.

From the obtained data on X-ray diffraction intensity, the hydrous crystalline potassium salt of ascorbic acid 2-glucoside was considered to have a molecular formula of $C_{12}H_{24}K_2O_{15}$, a structural formula of $C_{12}H_{17}O_{11}^-·2K^+·OH^-·3H_2O$, and a molecular wright of 486.51. As shown in FIG. 4, the crystal was estimated to be composed of one molecule of ascorbic acid 2-glucoside with hydrogen dissociated from the hydrogen group at position 3 of L-ascorbic acid, two potassium ions, one hydroxide ion, and three molecules of water.

The following examples explain the present invention in more detail, however, they should never restrict the present invention.

Example 1

<Hydrous Crystalline Potassium Salt of Ascorbic Acid 2-Glucoside>

One kilogram of particulate composition containing anhydrous crystalline ascorbic acid 2-glucoside (product name "AA2G" (registered trademark), with a purity of ascorbic acid 2-glucoside at least 98% by mass, commercialized by Hayashibara Co., Ltd., Okayama, Japan), was completely dissolved by the addition of 2 L of 5 N potassium hydroxide aqueous solution and the stirring. The mixed solution was added with 3 L of methanol, mixed, added with 10 g of crystalline of potassium salt by previously prepared by the method of Experiment 1 as seed crystal. After stirring and mixing, the resulting solution was allowed to stand at 5° C.

for 3 days to precipitate crystals. The obtained crystals were then collected by filtration, washed with 60% by volume methanol aqueous solution, and dried at 30° C. to produce about 1.1 kilograms of hydrous crystalline potassium salt of ascorbic acid 2-glucoside. The purity of ascorbic acid 2-glucoside in the crystal was 99.2% by mass when measured by HPLC method described in Experiment 2-2, the moisture of the crystal was 12.5% by mass when measured by Karl Fischer method, and the potassium content of the crystal was 14.1% by mass when calculated based on the result of ion chromatography. The product is a hydrous crystalline potassium salt of ascorbic acid 2-glucoside product with good flowability, and can be widely and advantageously used in various compositions such as food and beverage, cosmetics, quasi-drugs, and pharmaceuticals.

Example 2

<A Particulate Composition Containing Hydrous Crystalline Potassium Salt of Ascorbic Acid 2-Glucoside>

Seven parts by mass of tapioca starch was added to 25 part by mass of water and then dissolved therein by heating after the addition of a commercialized starch-liquefying enzyme. The solution was admixed with 3 parts by mass of L-ascorbic acid and adjusted to pH 5.5 to give a substrate solution. The substrate solution was admixed with the enzyme agent of CGTase from *Geobacillus thermophllus* (produced by Hayashibara Co., Ltd., Okayama, Japan) in an amount of 100 units per gram of the tapioca starch and enzymatically reacted at 55° C. for 50 hours to form ascorbic acid 2-glucoside and ascorbic acid 2-glycoside.

After inactivating the enzyme by heating the reaction solution, the solution was adjusted to pH 4.5, admixed with "Glucozyme #20000", a product name of a glucoamylase specimen (20,000 units/g), commercialized by Nagase ChemeteX Corp., Osaka, Japan, in an amount of 50 units per gram of the starch, and reacted at 55° C. for 24 hours to degrade ascorbic acid 2-glycoside into ascorbic acid 2-glucoside and to degrade the concomitant saccharides into D-glucose. The content of ascorbic acid 2-glucoside in the reaction solution was about 30.5% by mass, on a dry solid basis.

After inactivating the enzyme by heating, the reaction solution was decolored and filtered with an activated charcoal. The filtrate was desalted with a cation-exchange resin (H*-form), and subjected to an anion-exchange resin (OH⁻-form) to adsorb L-ascorbic acid and ascorbic acid 2-glucoside thereupon, followed by washing the resin with water to remove most of glucose and eluting the adsorbed ingredients with 0.5 N hydrochloric acid solution. The elute was concentrated and subjected to a gel filtration column chromatography using "DOWEX 50WX4" ($Ca^{2+}$-form), a product name of a strong-acid cation-exchange resin commercialized by Dow Chemical Co., Midland, USA, to collect a fraction rich in ascorbic acid 2-glucoside. The collected solution containing ascorbic acid 2-glucoside had a composition of 95.3% by mass of ascorbic acid 2-glucoside, 1.2% by mass of L-ascorbic acid, 2.5% by mass of D-glucose, and 1.0% by mass of other, on a dry solid basis.

The solution containing ascorbic acid 2-glucoside was concentrated under a reduced pressure to give a solid concentration of about 60% by mass, dissolved by adding potassium hydroxide to give a final concentration of 5 N, and further admixed with ethanol to give a final concentration of 60% by volume. Then, the solution was placed in a crystallizer, cooled to 5° C., admixed with a particulate composition containing hydrous crystalline potassium salt of ascorbic acid 2-glucoside obtained in Experiment 1, as a seed, in an amount of 2% by mass of the solid content of ascorbic acid 2-glucoside, and gently stirred and crystallized for 3 days to obtain a massecuite with precipitated hydrous crystalline potassium salt of ascorbic acid 2-glucoside. The massecuite was in usual manner subjected to a basket-type centrifuge to collect crystals, which were then sprayed with a small amount of 75% by volume ethanol solution for washing, pulverized and dried to obtain a particulate composition containing hydrous crystalline potassium salt of ascorbic acid 2-glucoside. The purity of ascorbic acid 2-glucoside of the product was 98.6% by mass, on a dry solid basis, the moisture of the product was 14.3% by mass when measured by Karl Fischer method, and the potassium content of the product was 14.1% by mass when calculated based on the result of ion chromatography.

The product is a hydrous crystalline potassium salt of ascorbic acid 2-glucoside product with good flowability, and can be widely and advantageously used in various compositions such as food and beverage, cosmetics, quasi-drugs, and pharmaceuticals.

Example 3

<A Composition of Hydrous Crystalline Potassium Salt of Ascorbic Acid 2-Glucoside and Anhydrous Crystalline Ascorbic Acid 2-Glucoside>

Fifty parts by mass of a hydrous crystalline potassium salt of ascorbic acid 2-glucoside obtained by the method in Example 1 was admixed to homogeneity with 50 parts by mass of particulate composition containing anhydrous crystalline ascorbic acid 2-glucoside (product name "AA2G" (registered trademark), commercialized by Hayashibara Co., Ltd., Okayama, Japan), pulverized and dried to obtain a powdered composition.

The product is a composition of a hydrous crystalline potassium salt of ascorbic acid 2-glucoside and a frequently used particulate composition containing anhydrous crystalline ascorbic acid 2-glucoside, and similarly as in conventional particulate composition containing anhydrous crystalline ascorbic acid 2-glucoside, it can be advantageously used as a cosmetic material, as well as a base material for quasi-drugs, pharmaceuticals, foods etc. Since the product exhibits a weak acidity when in an aqueous solution form, it facilitates the pH adjustment of final products to a desired pH compared to the use of conventional particulate compositions containing anhydrous crystalline ascorbic acid 2-glucoside.

Example 4

<Cosmetic Lotion>
(Formulation)

| | Ingredient | (% by mass) |
|---|---|---|
| (1) | Glycerin | 4.0 |
| (2) | Propylene glycol | 3.0 |
| (3) | 1,2-Pentane diol | 0.1 |
| (4) | A composition obtained by the method in Example 3 | 2.0 |
| (5) | Polyoxyethylene (20 moles) olein alcohol | 0.5 |
| (6) | Saxifraga stolonifera (beefsteak geranium) extract | 2.0 |

-continued

| | Ingredient | (% by mass) |
|---|---|---|
| (7) | Ethanol | 5.0 |
| (8) | Flavor | q.s. |
| (9) | Refined water | Remaining |

The ingredients (1) to (4) in the above formulation were dissolved in refined water (9) and then gradually admixed with a mixture of the ingredients (5) to (8) to obtain a cosmetic lotion. The product is a lotion that contains ascorbic acid 2-glucoside and is useful as an anti-ageing cosmetic lotion that has an improved anti-wrinkle or anti-fine-wrinkle action, as well as having a skin-whitening, anti-blemish, or anti-sagging skin action, and maintaining or promoting the barrier function and the hyaluronic acid production in the skin. Since the product contains 1,2-pentanediol, it has a satisfactory antiseptic effect and a moisture-retaining ability, as well as having a lesser skin stimulation and being excellent stability.

Example 5

<Essence>
(Formulation)

| | Ingredient | (% by mass) |
|---|---|---|
| (1) | Maltitol | 7.5 |
| (2) | A composition obtained by the method in Example 3 | 3.0 |
| (3) | 1,2-Alkanediol | 5.0 |
| (4) | Polyethylene glycol 1500 | 1.0 |
| (5) | Ethanol | 5.0 |
| (6) | Carboxy vinyl polymer | 0.4 |
| (7) | Sodium polyacrylate | 0.1 |
| (8) | Polyoxyethyleneoleylether (20 E.O.) | 1.5 |
| (9) | Olea europaea [olive] oil | 0.2 |
| (10) | Dipotassium glycyrrhizate | 0.1 |
| (11) | Potassium hydroxide | q.s. |
| (12) | Flavor | q.s. |
| (13) | Refined water | Remaining |

According to the above formulation, the ingredients were mixed in usual manner to obtain an essence. The product is an essence that contains ascorbic acid 2-glucoside and is useful as an anti-ageing serum that exerts a stable anti-wrinkle or anti-fine-wrinkle action, has an improved skin-whitening action, and has a satisfactory feeling of use.

Example 6

<Supplemental Health Food>
One part by mass of a composition obtained by the method in Example 3 was admixed to homogeneity with 99 parts by mass of trehalose (product name "TREHA" (registered trademark), commercialized by Hayashibara Co., Ltd., Okayama, Japan), then the mixture was filled into glass bottles of 50 g each to make the product. The product is useful as a supplemental health food fortified with vitamin C.

Example 7

<Health Food>
85 parts by mass of skimmed milk, 3 parts by mass of powdered skim milk, 6 parts by mass of trehalose (product name "TREHA" (registered trademark), commercialized by Hayashibara Co., Ltd., Okayama, Japan), 0.1 parts by mass of agar, 3 parts by mass of a composition obtained by the method in Example 3, 4 parts by mass of powdered glycosylated hesperidin, and 2 parts by mass of purified water were placed in the preparation tank and dissolved completely by heating to 55° C. with stirring. Then, the mixture was homogenized in usual manner, sterilized by a sterilizing cooler, and inoculated with 3% by mass of starter. The resulting mixture was filled into a plastic container and then fermented at 37° C. for 5 hours to obtain a yogurt-type health food. The product is a yogurt-type health food fortified with vitamin C.

Example 8

<Powdered Preparation of Vitamin C>
A composition obtained by the method in Experiment 3 for use as a powdered material for food products, was admixed with 70 parts by mass of sucrose, 10 parts by mass of dextrin, and an adequate amount of a flavor, followed by mixing the resulting mixture by a mixer into a powdered preparation of vitamin C. The product can be prepared by easily mixing to homogeneity a particulate composition containing crystalline ascorbic acid 2-glucoside with other powder by using a mixer without causing any troublesome event during its preparation step.

The product can be easily mixed with other materials for food products and it is a powdered preparation of vitamin C substantially free from causing coloration or solidification even when stored for a relatively long period of time. Since the product and compositions containing the same have the physiological functions of vitamin C, they can be orally taken to maintain the health or the whitening of the skin or the mucosa.

Example 9

<Ointment>
One part by mass of sodium acetate trihydrate, 4 parts by mass of DL-calcium lactate and 10 parts by mass of glycerin were mixed to homogeneity, and the mixture was added to another mixture of 50 parts by mass of vaseline, 10 parts by mass of vegetable wax, 10 parts by mass of lanolin, 14.5 parts by mass of sesame oil, 1 part by mass of a composition obtained by the method in Experiment 3 and 0.5 parts by mass of peppermint oil, and mixed to homogeneity to obtain an ointment.

The product is favorably usable as a sun-screening, skin-refining agent, skin-whitening agent and promoter for healing injury and burn.

INDUSTRIAL APPLICABILITY

The hydrous crystalline potassium salt of ascorbic acid 2-glucoside of the present invention is in the form of a novel crystalline ascorbic acid 2-glucoside that has not been known so far. In the case of using crystalline potassium salt of ascorbic acid 2-glucoside and anhydrous crystalline ascorbic acid 2-glucoside in combination, an appropriate control of the ratio of the above ingredients enables the pH adjustment of final products to a pH within a desired pH range, without neutralizing ascorbic acid 2-glucoside with an alkali; whereby food and beverage, cosmetics, quasi-drugs, pharmaceuticals, and industrial goods, according to the present invention, can be readily produced with a lesser

EXPLANATION OF SYMBOLS

In FIG. 2, the symbols mean as follows:
↓: A characteristic diffraction peak in a powder X-ray diffraction pattern of crystal
a: A diffraction peak at a diffraction angle (2θ) of 8.27°;
b: A diffraction peak at a diffraction angle (2θ) of 8.81°,
c: A diffraction peak at a diffraction angle (2θ) of 16.05°;
d: A diffraction peak at a diffraction angle (2θ) of 18.88°; and
e: A diffraction peak at a diffraction angle (2θ) of 25.64°.

In FIG. 3, the symbols mean as follows:
A: A powder X-ray diffraction pattern of a newly obtained crystal;
B: A powder X-ray diffraction pattern of potassium salt of ascorbic acid 2-glucoside (hydrous crystal);
C: A powder X-ray diffraction pattern of hydrous crystalline of ascorbic acid 2-glucoside (½ hydrous crystal);
D: A powder X-ray diffraction pattern of anhydrous crystalline of ascorbic acid 2-glucoside.

The invention claimed is:

1. A crystalline potassium salt of 2-O-α-D-glucosyl-L-ascorbic acid.

2. The crystalline potassium salt of 2-O-α-D-glucosyl-L-ascorbic acid of claim 1, which has at least diffraction peaks at diffraction angles (2θ) of 8.27°, 8.81°, 16.05°, 18.88°, and 25.64°, when measured by powder X-ray diffraction analysis.

3. The crystalline potassium salt of 2-O-α-D-glucosyl-L-ascorbic acid of claim 1, which is in a hydrous crystalline form.

4. A method for producing the crystalline potassium salt of 2-O-α-D-glucosyl-L-ascorbic acid of claim 1, comprising:

dissolving 2-O-α-D-glucosyl-L-ascorbic acid in a potassium hydroxide aqueous solution, wherein the molar ratio of potassium hydroxide to 2-O-α-D-glucosyl-L-ascorbic acid in the aqueous solution is 2.7 to 5.4;

adding an alcohol to the resulting solution such that the ratio of the alcohol to the 2-O-α-D-glucosyl-L-ascorbic acid is 3;

allowing the resulting mixture to stand; and collecting the precipitated crystalline potassium salt of 2-O-α-D-glucosyl-L-ascorbic acid in the mixture.

5. The method of claim 4, wherein said alcohol is methanol or ethanol.

6. A composition, which comprises the crystalline potassium salt of 2-O-α-D-glucosyl-L-ascorbic acid of claim 1.

7. The composition of claim 6, which further comprises an anhydrous crystalline 2-O-α-D-glucosyl-L-ascorbic acid, wherein the ratio of said anhydrous crystalline 2-O-α-D-glucosyl-L-ascorbic acid and said crystalline potassium salt of 2-O-α-D-glucosyl-L-ascorbic acid is in the range of 70:30 to 45:55 by mass.

8. The composition of claim 6, which is in the form of food and beverage, cosmetic, pharmaceutical, quasi-drug, or industrial product.

* * * * *